United States Patent [19]
Daskalakis

[11] Patent Number: 5,192,314
[45] Date of Patent: Mar. 9, 1993

[54] SYNTHETIC INTRAVENTRICULAR IMPLANTS AND METHOD OF INSERTING

[76] Inventor: Michael K. Daskalakis, 623 James Pl., Anaheim, Calif. 92801

[21] Appl. No.: 806,696

[22] Filed: Dec. 12, 1991

[51] Int. Cl.⁵ .......................... A61F 1/10; A61F 2/02
[52] U.S. Cl. ........................................ 623/3; 623/11
[58] Field of Search .................. 623/2, 11, 3, 1, 66; 604/96, 97, 98, 99

[56] References Cited

U.S. PATENT DOCUMENTS

| | | | |
|---|---|---|---|
| 3,279,464 | 10/1966 | Kline | 623/3 |
| 4,573,997 | 3/1986 | Wisman et al. | |
| 4,643,733 | 2/1987 | Becker | 623/11 X |
| 4,685,446 | 8/1987 | Choy | |
| 4,685,447 | 8/1987 | Iversen et al. | 623/11 X |
| 4,771,765 | 9/1988 | Choy et al. | |
| 4,820,303 | 4/1989 | Brauman | 623/11 X |
| 4,840,940 | 6/1989 | Sottiurai | 623/1 X |
| 4,902,273 | 2/1990 | Choy et al. | |
| 4,995,857 | 2/1991 | Arnold | |
| 5,005,591 | 4/1991 | Austad | 623/11 X |

Primary Examiner—Randall L. Green
Assistant Examiner—Dinh X. Nguyen
Attorney, Agent, or Firm—James G. O'Neill

[57] ABSTRACT

A synthetic intraventricular implant device adapted to be surgically secured in a ventricle of the heart of a patient. The shape, size and volume of the device so inserted will depend on the size of the ventricle of the patient, and how much of the end-diastolic volume thereof it is desired to reduce. The device is surgically inserted into and secured in place in the ventricle by suturing it onto a preselected segment of the interior wall of the ventricle to reduce end-diastolic volume, pressure and wall stress, and to subsequently increase ejection fraction and cardiac output. The device may include a fluid, liquid, semi-liquid, semi-solid, solid or viscous core and/or an inflatable balloon-like portion for use in assisting in the elimination of blood from the "dead volume" within the ventricle. Additionally, the inflatable implant, when used as a ventricular assist device, will increase the ejection fraction and contractility of the myocardium, as well as cardiac output, either permanently or temporarily, in some patients with specific cardimoypathies.

An implant device is inserted during open heart surgery on a patient, by forming an opening in a portion of the distal end wall of a ventricle of the patient's heart, inserting the selected implant into the interior chamber of the ventricle, suturing the implant in a predetermined position against a segment of the interior wall within the patient's ventricle and suturing the opening made in the distal end wall of the ventricle. Revascularization or associated procedures may follow or proceed insertion of the implant.

17 Claims, 2 Drawing Sheets

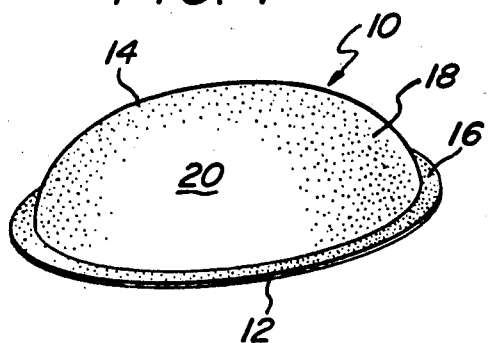
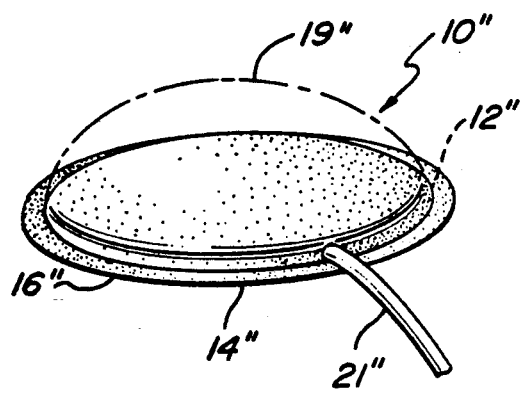
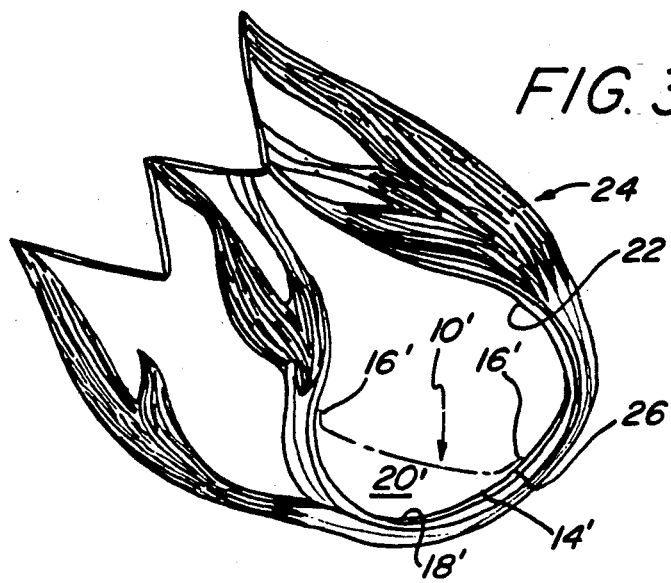
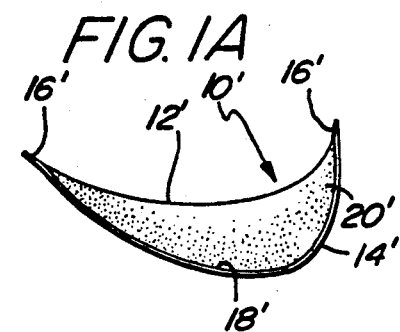
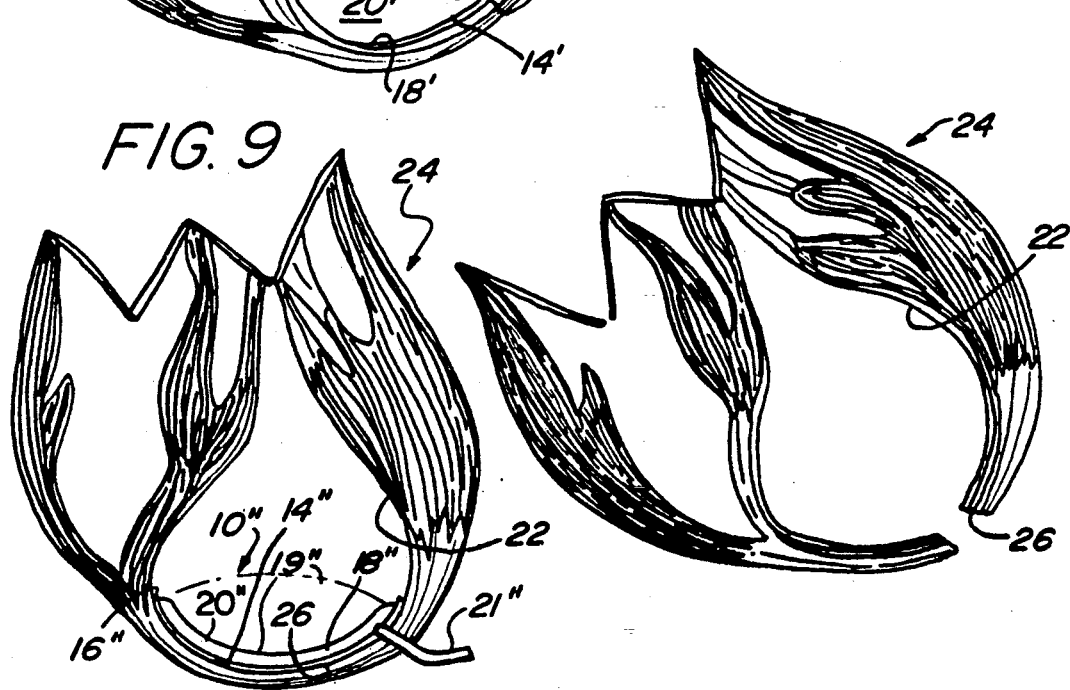

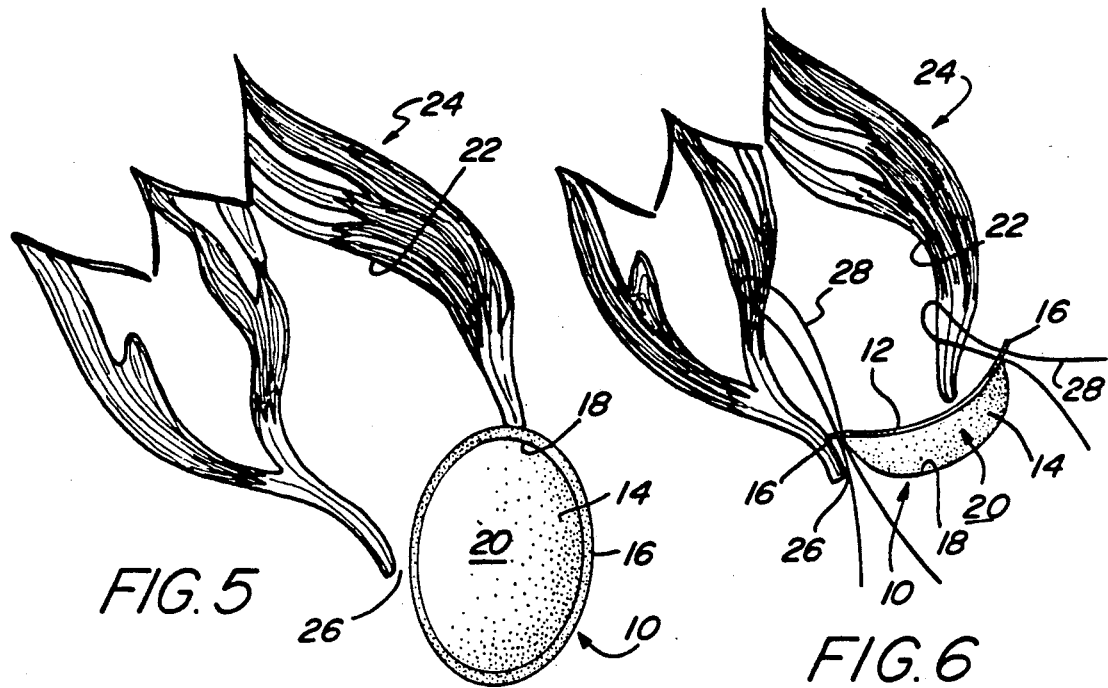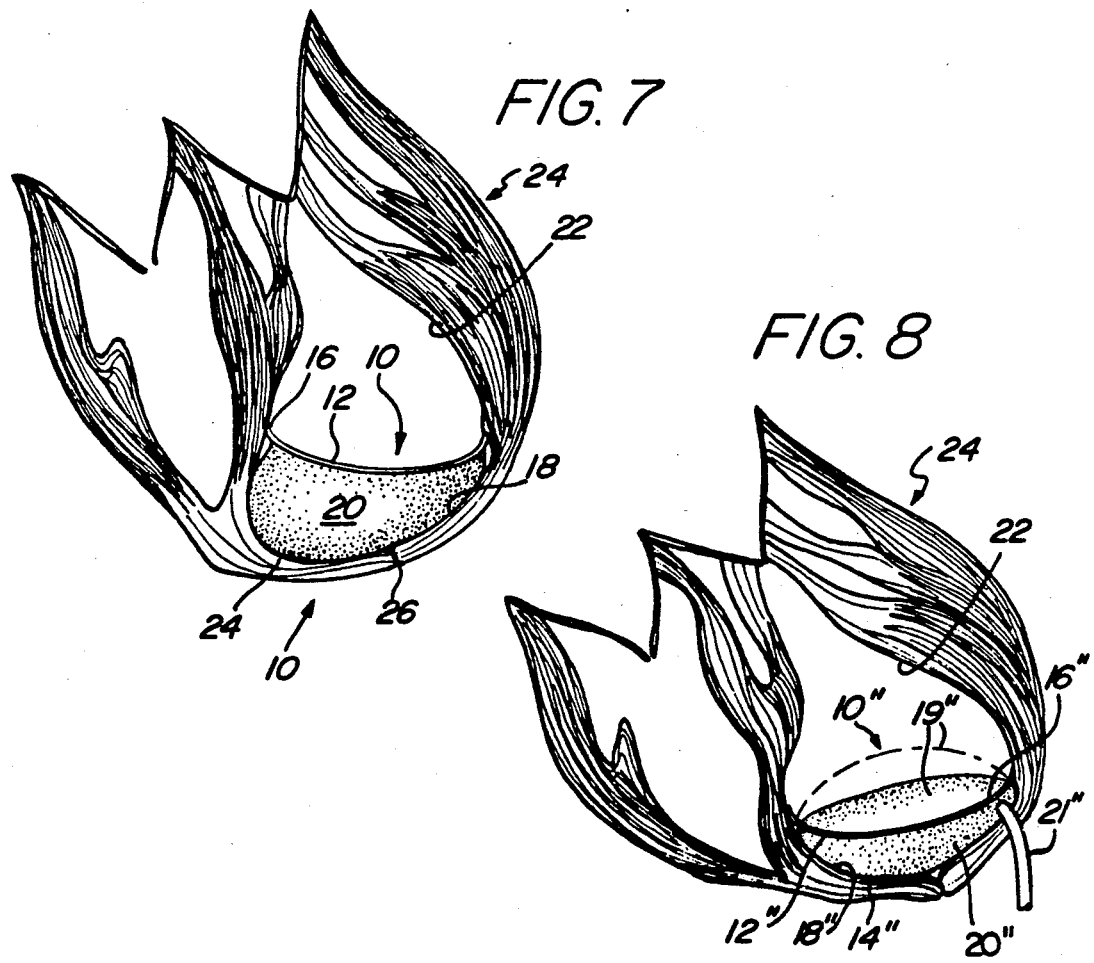

SYNTHETIC INTRAVENTRICULAR IMPLANTS AND METHOD OF INSERTING

BACKGROUND OF THE INVENTION

1. Field of the Invention

This invention relates generally to devices for the treatment of diseased hearts and more particularly to synthetic intraventricular heart implants and assist devices, and a method for inserting the same.

2. Description of Related Art

As is well known, the human heart has four main chambers. Of these chambers the left and right ventricles can be affected by many diseases that may need to be corrected by surgical procedures. By way of example only, and not for reasons of limitation, the present invention will be described with respect to the left ventricle of a patient's heart, from which blood is pumped into the aorta and then into the arteries of the human body. However, it is to be understood that the present invention is also applicable to the right ventricle (when assist devices are needed).

Recent studies have shown that many patients who suffer from heart diseases, such as arteriosclerosis with left or right ventricular dysfunction, and the like, and who undergo some type of revascularization surgery are provided with relief from angina. However, such revascularization procedures generally fail to improve ventricular function, particularly if a patient's left ventricle is enlarged. Such patients, therefore, continue to deteriorate with eventual heart failure, resulting in increased mortality and reduced chances of survival. This occurs, because of the increased end-diastolic volume and pressure, and low ejection fraction (expulsion of blood) from the left ventricle.

Medical therapy, after such revascularization procedures, with diuretics and ACE inhibitors, helps some patients, but does not significantly reduce mortality, nor does it increase the survival rate for patients. Therefore, there is a long standing need for a device and/or method to increase the survival rate of patients suffering from left ventricle enlargement and dysfunction, as well as other heart diseases, which require surgery.

While left and right ventricular assist devices and methods of using them are known, these known devices and methods only bring about limited relief in certain circumstances. These known devices and methods are not usually for permanent placement within the heart, nor do they satisfactorily produce results in all patients and/or all circumstances. Therefore, there still exists the need in the medical art for a device and method which may be used to permanently aid those patients who are suffering from heart diseases, such as, but not limited to, arteriosclerosis with left ventricle dysfunction in which evasive revascularization surgery must be performed.

One known assist device is shown in U.S. Pat. No. 4,573,997, which discloses a right ventricular assist device for aiding the circulation of blood from the right ventricle, for a predetermined time, until the patient's heart recovers sufficiently to remove the assist device. The device includes a smooth segmented sac having a single, valveless passageway/inlet and outlet. The sac is surrounded by a rigid ellipsoidal shell with a first opening for the inlet/outlet of the sac and a second opening for pressurizing a separate interior portion of the shell. A flexible diaphragm extends across the interior of the shell to divide the interior into two unequal volumes, with the sac and the first opening in a first and larger volume, and the second opening and a pressurizing chamber in a second and smaller volume. The diaphragm expels approximately 90% of the blood held in the sac when the smaller chamber is pressurized. The device is attached to the pulmonary artery of a patient and, therefore, is not useful in a ventricle, nor can it be inserted into the heart of a patient.

U.S. Pat. No. 4,685,446, discloses a method and device to assist the left ventricle of a patient, consisting of an inflatable balloon connected at the distal end of a single lumen catheter that is inserted into the left ventricle of the patient, and a pump at the proximate end of the catheter, to inflate and deflate the balloon by means of a fluid, upon receipt of an electronic signal that coincides with ventricular systole and diastole, to augment ejection of blood from the left ventricle. This device is a temporary device that requires insertion through the arteries of a patient, is not implantable, and both the device and the method disclosed therein do not, among other things, take into account the problems that occur because of weakened wall portions of a ventricle.

U.S. Pat. Nos. 4,771,765 and 4,902,273 are related to U.S. Pat. No. 4,685,446, discussed above. Both of these patents disclose similar assist devices and methods to assist the left, or both the left and right ventricles of the heart of a patient. However, the devices disclosed in these two patents include either one or two balloons connected at one or two distal ends of a two lumen catheter inflatable by a first lumen in the catheter, as well as an intraaortic balloon located between the proximal and distal end (or ends) of the catheter and inflatable by the second lumen. If only one distal balloon is used, it is inserted into the left ventricle, however, if two distal balloons are used, they are inserted into both the left and the right ventricles. A pumping mechanism, having two pumps, is provided at the proximate end of the catheter, to inflate and deflate the balloons on the devices by means of a fluid, at pre-determined times. These devices and methods are complicated, and suffer from the same drawbacks as U.S. Pat. No. 4,685,446.

U.S. Pat. No. 4,995,857, discloses a left ventricular assist device and method to relieve the hemodynamic burden on a diseased left ventricle by inserting a shunt having an impeller for substantially non-turbulent, non-traumatic flow of blood either from the left atrium or the patient's venous system, directly into the patient's arterial system. The device of this patent may be implanted temporarily or permanently in a patient, to by-pass the left ventricle, but is not an intra-ventricular device, and is always implanted exteriorly of the heart itself.

The above-mentioned devices and methods provide limited improvements for certain heart diseases, as described in the respective patents. However, the devices and methods of these patents fail to adequately work in all patients under all circumstances, tend to be complex, are not implanted within a ventricle of a patient, and are limited to the specific applications set forth therein.

SUMMARY OF THE INVENTION

The present invention is directed to a device and method for use in or to permanently assist the damaged heart of a patient, particularly the left or right ventricles, after revascularization surgery so as to greatly improve the efficiency and operation thereof and thereby enhance the patient's health and chances of survival after such surgery.

It is, therefore, a general object of the present invention to eliminate the stagnant pool of blood or "dead volume" in the ventricles of a diseased human heart. It is a more particular object of the present invention to eliminate the "dead volume" in the ventricles of a diseased human heart, by surgical means. It is a further object of the present invention to eliminate the "dead volume" in the ventricles of a diseased human heart by implanting specifically shaped and contoured, space occupying devices within "such ventricles". And, it is a still more particular object of the present invention to provide a method for operating on a diseased ventricle to eliminate the "dead volume" therein by inserting a space occupying device therein, and securing this device in position.

Therefore, in a preferred embodiment of the present invention, the device used is a synthetic intraventricular implant device that is surgically secured in a ventricle of the heart of a patient. The shape and contour of the implant device varies both in size and volume, depending on predetermined conditions, such as the size of the ventricle of the patient, the anatomic location of the device and how much of the end diastolic volume thereof it is desired to reduce. The implant device is inserted into and secured in place in the ventricle, on a segment or segments of the interior wall, or to replace a resected segment of the wall, where there is marked dyskinesia or akinesia, by suturing it into position to thereby reduce end-diastolic volume and pressure, as well as wall stress. and subsequently, to increase ejection fraction and cardiac output. The implant device may include an inflatable balloon-like portion and/or a solid, soft or expandable core, to eliminate blood from the "dead volume" within the ventricle. The inflatable balloon portions of the implant devices can be used as ventricular assist devices, with proper connection to a skeletal muscle, an external motor console, or to a microminiature pneumatic or hydraulic energy convertor, that will be implanted into the abdomen of a patient. The skeletal muscle will contract, in a manner known to those skilled in the art to move the implant into the ventricle cavity, or the actuator will transfer electrical energy via high frequency induction from an externally worn rechargeable battery source, across intact skin to an implanted secondary coil, so that nothing penetrates the body surface. The actuator will then convert the electrical energy into mechanical energy used by a pump to inflate the balloon portion of the implant, synchronous with the systolic function of the heart.

The preferred method for inserting an implant in a patient comprises the steps of performing open heart surgery on the patient; opening a portion of the distal end wall of the ventricle of the patient's heart; either resecting the diseased portion of the heart and replacing it with the implant, or inserting the selected implant into the interior of the ventricle chamber; suturing the implant in the predetermined selected position within the resected wall, or the interaval cavity of the patient's ventricle; and suturing the opening made in the distal end wall of the heart.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 1 is a perspective view of one embodiment of an implant device of the present invention;

FIG. 1a is a side elevational view of a further embodiment of an implant device of the present invention;

FIG. 2 is a perspective view of a still further embodiment of an implant or assist device of the present invention;

FIG. 3 is partial cross sectional view of a human heart showing the left ventricle with the implant device of FIG. 1a shown in broken line, inserted therein;

FIG. 4 is a partial cross sectional view of a human heart, similar to FIG. 3, with a cut in the distal end of the left ventricle;

FIGS. 5 through 7 show the preferred method for inserting and securing an implant or assist device through an opening formed in the distal end of the left ventricle of FIG. 4, by first inserting the device through the opening, suturing the implant device in place, and suturing the opening back together;

FIG. 8 shows one embodiment of an expandable implant or assist device secured in place within a left ventricle; and FIG. 9 shows another embodiment of an expandable implant or assist device secured in place within a left ventricle.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for implants and a method for treating a diseased heart.

It is now believed that the main reason for the current lack of cure or improvement in many patients after revascularization surgery is the already established or existing cardiomegaly with its hemodynamic effects on the left ventricle function. In particular, in patients who must have revascularization surgery, the increased end-diastolic volume and pressure which cause increased stresses on the wall of the left ventricle, the low ejection fraction and resulting low cardiac output cannot be reversed by the revascularization procedure or medication in all patients. This has been shown to be the case in laboratory tests of patients using a ventriculogram. In accordance with the coronary artery or arteries involved, the left ventricle exhibits dysfunction (hypokinesis or akinesis) in the distal half thereof, while the basal parts contract somewhat satisfactorily to sustain life in most of these patients. The blood that remains in the distal part of the left ventricle and which is not expelled, during systole, forms a stagnant pool of blood referred to as "dead volume".

For example, following severe ischemia or myocardial infarction (ventricular mass damage not less than 20%) a vicious cycle of pathophysiologic events takes place. The left ventricle dilates to maintain stroke volume and cardiac output. This dilation affects and the non-infarcted parts of the left ventricle, thus increasing the stress on the walls of the left ventricle (La Place law, T=Pr). Hemodynamically, the end-diastolic volume and pressure increase, and along with the increased wall stress, produces further ischemia to the endocardium and an increase in the oxygen demand. All of these factors result in reduced contractility, low ejection fraction and low cardiac output, which if continued, results in cardiac decompensation.

A study of 57 patients whose ejection fraction ("EF") was less than 35% was performed in the Cardiology Department at the Hippokration General Hospital, University of Athens, in Athens Greece. This study included the taking of a patient's history, coronary angiogram and ventriculogram, and showed that the majority of the patients would benefit from the combined approaches disclosed herein; namely, revascularization of the myocardium and the placement of an intraventricular implant in the left ventricle. The study was based on reviewing the ventriculogram and evaluation of the left ventricular function and coronary anatomy of each of the patients. More details could, of course, be obtained by studying these patients with an echo cardiogram, both before and after exercise, to identify the exact extent of dysfunction of the left ventricle as well as the intraventricular septum contractility.

Certain patients with arteriosclerotic occlusive disease of the coronary arteries, with and without infarction, have clinical signs of angina, congestive heart failure, or both. When the left ventricle of such patients is dilated, the end-diastolic pressure and volume are increased, while their EF is low and their cardiac output is reduced. Revascularization alone on these patients will improve their angina, but will do very little, if anything, to stop the process of progressive deterioration of the left ventricular function.

To correct this problem, the intraventricular implants of the present invention, along with revascularization, will improve ventricular function by reducing the end-diastolic volume and pressure, and wall stress therein, and by increasing the EF and cardiac output of the left ventricle, since it increases the contractility of the remaining segments of the left ventricle.

By surgically inserting the implants of the present invention in the left ventricle during revascularization surgery required in a patient, the "dead volume" where stagnant blood would normally pool or accumulate during the cardiac cycle (mainly during diastole), is eliminated. Additionally, this is done without altering the stereo-geometric configuration of the left ventricle that is necessary for more efficient functioning thereof, to improve the function of the left ventricle by reducing end-diastolic volume and pressure, while increasing contractility, EF and cardiac output. Also, the inflatable implant devices of the present invention, which are to be used as ventricular assist devices (specifically manufactured to predetermined specifications) will act in the same manner to eliminate the stagnant blood or "dead volume". Furthermore, movement of the balloon of an implant by the skeletal muscle, or inflation of the balloons of such assist devices, by means of the above-mentioned pump during each systole, will aid the left ventricle function by increasing the ejection fraction, cardiac output and contractility of the myocardium.

Turning now to the drawings, and specifically FIGS. 1, 1a and 3-7, there shown are two embodiments of an implant 10, 10' for insertion into a ventricle of a human heart. The implant 10 shown in FIG. 1 is contoured and shaped for insertion in position on the apical wall of the internal cavity of the left ventricle of a patient; while the implant 10', shown in FIG. 1a, and in broken line in FIG. 3 is contoured and shaped for insertion on or to replace a resected dyskinetic or akinetic segment of the antero-lateral, or postero-apical wall thereof. These implants 10 and 10' are comprised of an elongated, generally oblong, or oval shaped body, having inner and outer walls 12, 12' and 14, 14', sealingly fixed together, with a surrounding cuff or rim 16, 16' and a hollow, internal chamber or portion 18, 18'. Each implant 10, 10' is specifically shaped, sized and contoured to fit in and fill a specified volume of space within a ventricle cavity or chamber, and to either replace the resected segment on the wall or follow the contours of a selected segment of the internal wall of the cavity into which it is implanted. The implants 10 and 10', therefore, are made in various shapes and sizes with variable dimensions, depending on a patient's requirements, and where it is to be secured within a ventricle. Each implant 10, 10' including the respective walls 12, 12' and 14, 14' and the cuff 16, 16', may be fabricated in any known manner, from any known flexible or semi-rigid, synthetic, non-allergenic, bio-acceptable material for use within the human body. Materials, such as Dacron, Polytetrafluroethylene (PTFE), or the like are now widely used for devices that are inserted into the human body, and could be used herein. The inner wall 12, 12' may be covered with pericardium of proportional size.

In some embodiments of the implants 10, 10' the walls 12, 12' and 14, 14' are woven from Dacron and, if desired they may be saturated with a protein or impregnated with heparin. The cuff 16, 16' is preferably formed by an extended portion of the outer wall 14, 14' and completely surrounds the walls and the internal chamber 18, 18', at least around the periphery thereof, after the walls are sealed together in a manner known those skilled in the art. The internal chamber 18, 18' includes a fluid, liquid, semi-liquid, semi-solid, solid, or viscous core 20, 20' which is also formed from a non-allergenic, non-toxic and bio-acceptable substance.

In other embodiments of the implants 10, 10' the outer wall 14, 14' is made relatively thicker and the inner wall 12, 12' relatively thinner, and therefore, partially expandable. The walls 12, 12' and 14, 14' are then sealingly held together in any known manner, with a portion of the outer wall 14, 14' forming the cuff 16, 16' in such a manner that the inner wall 12, 12' may be partially expanded (in the nature of a balloon) so that varying amounts of a non-toxic, non-allergenic, non-embolizing water/blood soluble, bio-acceptable liquid or semi-liquid core or substance 20, 20' may be inserted and held within the internal chamber 18, 18'. The liquid filled implant is especially useful to replace a resected segment of the wall, and to be acted upon by a contracting skeletal muscle.

In still other embodiments of the invention, as shown more clearly in FIGS. 2, 8 and 9, an implant 10" is provided with inner and outer walls 12", 14", sealingly fixed together, at least around the periphery thereof, with a surrounding cuff or rim 16". The inner wall 12" may be expandable itself, or a separate inflatable portion or balloon 19" may be secured to the outer surface of the inner wall 12". The wall 12" itself, or the balloon 19", is then expandable or inflated outwardly, away from the outer wall 14", and, if applicable, inner wall 12", as shown in broken line in FIGS. 2, 8 and 9, to act or serve as an implant and/or assist device. The outer and inner walls may also include a hollow, internal chamber or portion 18" therebetween (see FIG. 9), having inserted therein, a selected core or substance 20″, similar or identical to the core or substance 20, 20′ in implants 10, 10′. A tube 21″ having a lumen therein is fluidly connected to the inflatable inner wall 12″ or hollow balloon 19″ so as to inflate the same, during each ventricular contraction, by pump means, described above but not shown, in a manner known to those skilled in the art. The implant or assist device 10″ is then secured in position within the left or right ventricle so that expansion of the wall or balloon is specifically aligned with or directed toward an exit, such as the aortic valve in the left ventricle, or the pulmonic valve in the right ventricle, so as, for example, to force blood in the "dead volume" out through the open aortic valve during systole. This will increase heart stroke volume and cardiac output, while the reduced end-diastolic volume and pressure caused thereby will improve the ventricular function.

As shown more clearly in FIGS. 3, 6, 7 and 8 the core or substance 20, 20′, or 20″ that fills interior chamber 18, 18′ or 18″ helps to shape and contour both the inner (facing toward the ventricle chamber) and outer surfaces (held against the interior wall of the ventricle chamber or replacing the resected segment of the ventricle wall) of the implant 10, 10′, or 10″ so as to allow the implant/assist device to be surgically inserted and secured within a predetermined or selected segment of a left ventricle 22 of a heart 24 to meet the varying and different requirements of patient's hearts. Specifically, the implants 10, 10′, 10″ are designed to be placed in and snugly secured against specific interior wall segments, or replace a resected wall segment within the left ventricle chamber to fill all, or as much as is possible of, the "dead volume" and to eliminate the pooled blood volume in these areas. The "dead volume" is evaluated or measured by a ventriculogram and an echo cardiogram taken along different planes, with or without exercise by the patient. The specific shape, size and volume of the implant to be used on a patient will also depend on the end-diastolic volume that is to be reduced. In the expandable or inflatable embodiments of the invention, the volume to be injected into the expandable wall 12″ or inflatable balloon 19″ thereof, will be based on an esophageal echocardiogram taken during surgery, and when the heart has resumed its contractibility. The specific size and shape of the implant to be used will also depend on the actual disease or damage to segments of the ventricle of the patient being operated on.

The preferred method of inserting the implant devices of the present invention within a ventricle requires open heart surgery. Sometime during such surgery, as determined by a surgeon, an implant, implants and/or an assist device is surgically implanted in the left or right ventricle, with only the left ventricle shown in FIGS. 3-9 of the drawings, for reasons of simplicity. As shown most clearly in FIG. 4, the distal end portion or end wall of the left ventricle of a patient's heart 24 is cut, along a line to form an opening 26, or resect a portion of the wall. A selected implant or assist device is then inserted through opening 26, or into the resected portion of the wall into the interior chamber 22 of the left ventriclle (See FIG. 5). Suturing material 28 is passed through the cuff of the implant or assist device (See FIG. 6), and the implant or assist device is then sutured into a predetermined, selected position against a segment of the interior wall, within the patient's left ventricle chamber, such as in the apical, antero-lateral, or postero-apical positions, or in the resected segment of the wall. The implants in the resected wall are covered by skeletal muscle, or the cut or opening 26 is then sutured closed or shut (See FIGS. 3 and 7-9).

What has been shown and described is a new and improved synthetic intraventricular implant devices capable of being surgically secured against selected segments of damaged walls in the internal cavity of a ventricle of a patient's heart during open-heart surgery, by a method which enables a surgeon to quickly, safely and expeditiously insert the desired implant device(s) in a preselected position(s).

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A synthetic intraventricular implant device capable of being surgically secured within a ventricle of a human heart, said ventricle having a wall with exterior and interior surfaces and an interior cavity with a distal end, comprising:

a generally oblong, shaped and contoured body having an inner wall adapted to face said interior cavity of said ventricle and an outer wall adapted to be snugly secured against said interior surface of said ventricle;

said inner and outer walls of said contoured body being sealingly fixed together; and a cuff formed from a portion of one of said inner and outer walls of said contoured body so as to completely surround said inner and outer walls of said contoured body for securing said implant in position within said wall of said ventricle, with said cuff capable of being fixed to said interior surface of said ventricle wall, within said interior cavity.

2. The synthetic intraventricular implant device of claim 1 wherein said ventricle is a left ventricle and said implant is inserted into a resected segment of said ventricle wall with said outer wall of said implant snugly secured against a surface of skeletal muscle whereby said implant may be displaced into said interior cavity of said left ventricle upon contraction of said skeletal muscle.

3. The synthetic intraventricular implant device of claim 1, further including a hollow, internal chamber formed between said inner and outer walls of said contoured body and a core of material held within said internal chamber.

4. The synthetic intraventricular implant device of claim 3 wherein said inner and outer walls are made from a material selected from the group consisting of Dacron, Polytetrafluroethylene and other synthetic, non-allergenic, bio-acceptable materials for use within a human body.

5. The synthetic intraventricular implant device of claim 3 wherein said core of material is selected from a group consisting of synthetic, non-allergenic, bio-acceptable fluids, liquids, semi-liquids, semi-solids and solids.

6. The synthetic intraventricular implant device of claim 3, further including an expandable balloon fixed to said inner wall, and a tube fluidly connected to said expandable balloon.

7. The synthetic intraventricular implant device of claim 1, further including an expandable balloon fixed to said inner wall of said contoured body, and a tube fluidly connected to said expandable balloon.

8. The synthetic intraventricular implant device of claim 1 wherein said inner wall of said contoured body is expandable and a tube is fluidly connected thereto.

9. The synthetic intraventricular implant device of claim 1 wherein said cuff is formed from a portion of said outer wall of said contoured body extending beyond said inner wall thereof and said inner wall thereof is capable of being covered with pericardium.

10. The synthetic intraventricular implant device of claim 1 wherein said inner and outer walls of said contoured body are made from a material selected from the group consisting of Dacron, Polytetrafluroethylene and other synthetic, non-allergenic, bio-acceptable materials for use within a human body.

11. A synthetic intraventricular implant device capable of being surgically secured in a ventricle of a human heart, which ventricle has a wall with exterior and interior surfaces and an interior cavity formed therein having a distal end, comprising:
   a generally oblong, shaped and contoured body having an inner wall adapted to face said interior cavity of said ventricle and an outer wall adapted to be snugly secured against a predetermined segment of said interior wall of said ventricle interior cavity; said inner and outer walls of said contoured body being sealingly fixed together around a periphery;
   a hollow, internal chamber formed within said periphery between said inner and outer walls of said contoured body;
   a core of material held within said internal chamber of said contoured body; and
   a cuff formed from a portion of one of said inner and outer walls of said contoured body so as to completely surround said periphery and said inner and outer walls of said contoured body for securing said implant in position within said interior cavity of said ventricle, with said cuff capable of being fixed to said interior wall of said ventricle.

12. The synthetic intraventricular implant device of claim 11 wherein said inner and outer walls of said contoured body are made from a material selected from the group consisting of Dacron, Polytetrafluroethylene and other synthetic, non-allergenic, bio-acceptable materials for use within a human body.

13. The synthetic intraventricular implant device of claim 11 wherein said core of material held within said internal chamber of said contoured body is selected from a group consisting of synthetic, non-allergenic bio-acceptable fluids, liquids, semi-liquids, semi-solids and solids.

14. The synthetic intraventricular implant device of claim 13 wherein said inner wall of said contoured body is expandable.

15. The synthetic intraventricular implant device of claim 11, further including an expandable balloon fixed to said inner wall of said contoured body, and a tube fluidly connected to said expandable balloon.

16. The synthetic intraventricular implant device of claim 11 wherein said inner wall of said contoured body is expandable and a tube is fluidly connected thereto.

17. The synthetic intraventricular implant device of claim 11 wherein said cuff is formed from a portion of said outer wall of said contoured body extending beyond said inner wall thereof and said inner wall thereof is covered with pericardium.

* * * * *